United States Patent [19]
Deluca et al.

[11] Patent Number: 5,952,317
[45] Date of Patent: *Sep. 14, 1999

[54] CALCITRIOL DERIVATIVES AND THEIR USES

[75] Inventors: Hector Floyd Deluca, Deerfield; Heinrich Konstantin Schnoes, Madison, both of Wis.

[73] Assignee: Wisconsin Alumni Research Foundation, Madison, Wis.

[ * ] Notice: This patent issued on a continued prosecution application filed under 37 CFR 1.53(d), and is subject to the twenty year patent term provisions of 35 U.S.C. 154(a)(2).

[21] Appl. No.: 08/531,403

[22] Filed: Sep. 21, 1995

[51] Int. Cl.$^6$ .................................................... A61K 31/59
[52] U.S. Cl. ............................................................ 514/167
[58] Field of Search .............................................. 514/167

[56] References Cited

U.S. PATENT DOCUMENTS

| | | | |
|---|---|---|---|
| 3,887,545 | 6/1975 | Iacobelli et al. | 260/239 |
| 3,928,397 | 12/1975 | Ikekawa et al. | 260/397 |
| 3,993,675 | 11/1976 | Uskokovic et al. | 260/397 |
| 4,006,172 | 2/1977 | Salmond | 260/397 |
| 4,195,027 | 3/1980 | DeLuca et al. | 260/397.2 |
| 4,225,596 | 9/1980 | Deluca | 424/236 |
| 4,310,467 | 1/1982 | Batcho et al. | 260/397 |
| 4,410,515 | 10/1983 | Holick et al. | 424/180 |
| 4,421,690 | 12/1983 | Partridge et al. | 260/397 |
| 4,428,946 | 1/1984 | DeLuca et al. | 424/236 |
| 4,568,491 | 2/1986 | Fürst et al. | 260/239 |
| 4,670,190 | 6/1987 | Hesse et al. | 260/397 |
| 4,691,032 | 9/1987 | Fürst et al. | 549/450 |
| 4,863,744 | 9/1989 | Urquhart et al. | 424/484 |
| 5,206,229 | 4/1993 | Calverley et al. | 514/167 |
| 5,246,925 | 9/1993 | Deluca et al. | 514/167 |
| 5,321,018 | 6/1994 | Deluca | 514/167 |

FOREIGN PATENT DOCUMENTS

| | | |
|---|---|---|
| A2530624 | 1/1984 | France . |
| A658050 | 10/1986 | Switzerland . |
| A2023146 | 12/1979 | United Kingdom . |
| A2026494 | 2/1980 | United Kingdom . |

OTHER PUBLICATIONS

Mallon et al, "Binding Specificity of the Rat Serum Vitamin D Transport Protein", Journal of Steroid Biochemistry, vol. 13, No. 4, pp. 409–413, 1980.

Tachibana, "Preparation of 1–Acyloxyvitamin D Derivatives as Pharmaceuticals", Chemical Abstracts, Abstract No. 231159, vol. 121, No. 19, Nov. 7, 1994.

Tachibana et al, "Preparation of Vitamin $D_2$ and Its Derivatives", Chemical Abstracts, Abstract No. 83752, vol. 121, No. 7, Aug. 15, 1994.

Morimoto et al, "Preparation of Vitamin $D_2$ and $D_2$ Derivatives and Intermediates", Chemical Abstracts, Abstract No. 171825, vol. 117, No. 17, Oct. 26, 1992.

Teijin LTD, "1α,24(s),25–Trihydroxycholecalciferol", Chemical Abstracts, Abstract No. 156875, vol. 100, No. 19, May 7, 1984.

Kobayashi et al, "Studies On Organic Fluorine Compounds. XXXIX. Studies on Steroids, LXXIX. Synthesis of 1α, 25–Dihydroxy–26,26,26,27,27,27–hexafluorovitamin $D_3$", Chemical and Pharmaceutical Bulletin, vol. 30, No. 12, pp. 4297–4303, 1982.

J. P. Bonjour et al, "Effect of Synthetic Vitamin D Derivatives on Calcium and Phosphate Metabolism in Intact Vitamin D–Replete Rats", Metabolic Bone Disease & Related Research, pp. 23–28, 1978.

Boris et al, "Structure–Activity Relationships of Compounds Related to Vitamin D", Endocrinol. Calcium Metab., 1982.

"Preparation of 1–acyloxyvitamin D Derivatives as Pharmaceuticals", Chemical Abstracts, vol. 121, No. 19, Nov. 7, 1994.

"Preparation of Vitamin $D_2$ and Its Derivatives", Chemical Abstracts, vol. 121, No. 7, Aug. 15, 1994.

"Preparation of Vitamin $D_2$ and $D_2$ Derivatives and Intermediates", Chemical Abstracts, vol. 117, No. 17, Oct. 26, 1992.

"1,α,24(s),25–Trihydroxycholecalciferol", Chemical Abstracts, vol. 100, No. 19, May 7, 1984.

"Studies on Organic Fluorine Compounds. XXXIX. Studies on Steroids. LXXIX. Synthesis of 1α,25–Dihydroxy–26,26, 26,27,27,27–Hexafluorovitamin $D_3$", Chemical and Pharmaceutical Bulletin, vol. 30, No. 12, 1982.

E.J. Semmler et al, The Synthesis of 1α,25–Dihydroxycholecalciferol—A Metabolically Active Form of Vitamin $D_3$, (1972), Tetrahedron Letters No. 40, pp. 4147–4150.

*Primary Examiner*—Theodore J. Criares
*Attorney, Agent, or Firm*—Andrus, Sceales, Starke & Sawall

[57] ABSTRACT

A method of treating metabolic bone diseases such as osteoporosis, as well as other disease states treatable with vitamin D compounds, comprises administering an effective amount of one or more modified vitamin D compound. The modified compound contains a typical vitamin D nucleus but with in vivo hydrolyzable groups at one or more of the 1, 3 and 25 carbon positions. The time of conversion of the modified compound to its active form, such as calcitriol, can be regulated to thus provide controlled release of the compound in vivo over time, by changing or modifying the hydrolyzable groups.

43 Claims, 1 Drawing Sheet

CALCITRIOL DERIVATIVES AND THEIR USES

STATEMENT REGARDING FEDERALLY SPONSORED RESEARCH OF DEVELOPMENT

This invention was made with United States government support award by the National Institutes of Health (NIH), Grant #DK-14881. The United States Government has certain rights in this invention.

BACKGROUND OF THE INVENTION

This invention relates to biologically active vitamin D compounds, and more particularly to vitamin D compounds with hydrolyzable groups at one or more of the 1, 3 and 25 carbon positions, such as esters of 1α,25-dihydroxyvitamin $D_3$ or esters of 1,25-dihydroxyvitamin $D_3$ analogs, and their use to regulate over time the function of $1,25(OH)_2D_3$ (or of $1,25(OH)_2 D_3$ analogs) during the treatment of a variety of diseases such as osteoporosis, renal osteodystrophy, hypoparathyroidism or proliferative skin disorders.

The 1α-hydroxylated metabolites of vitamin D—most importantly 1α,25-dihydroxyvitamin $D_3$ and 1α,25-dihydroxyvitamin $D_2$—are known as highly potent regulators of calcium homeostasis in animals and humans. With the discovery of 1α,25-dihydroxyvitamin $D_3$ as the active form of the vitamin has come an intense investigation of analogs of this hormonal form of vitamin D with the intent of finding analogs that have selective biological activity. As a consequence, many structural analogs of these metabolites, such as compounds with different side chain structures, different hydroxylation patterns, or different stereochemistry, have been prepared and tested. Important examples of such analogs are 1α-hydroxyvitamin $D_3$, 1α-hydroxyvitamin $D_2$, various side chain fluorinated derivatives of 1α,25-dihydroxyvitamin $D_3$, 19-nor-vitamin D compounds, and side chain homologated analogs. Several of these known compounds exhibit highly potent activity in vivo or in vitro, and some of these have been found to exhibit an interesting separation of activities in cell differentiation and calcium regulation. This difference in activity provides these compounds with advantageous therapeutic activity profiles and thus some of these compounds are in use, or have been proposed for use, in the treatment of variety of diseases such as renal osteodystrophy, vitamin D-resistant rickets, osteoporosis, psoriasis, and certain malignancies.

Various forms of osteoporosis are known, e.g., postmenopausal, senile and steroid-induced osteoporosis, one of the characteristics of which is the loss of bone mass. Females at the time of menopause suffer a marked loss of bone mass giving rise ultimately to osteopenia, which in turn gives rise to spontaneous crush fractures of the vertebrae and fractures of the long bones. This disease is generally known as postmenopausal osteoporosis and presents a major medical problem, both in the United States and most other countries where the life-span of females reaches ages of at least 60 and 70 years. Generally, the disease which is often accompanied by bone pain and decreased physical activity, is diagnosed by one or two vertebral crush fractures with evidence of diminished bone mass. It is known that this disease is accompanied by diminished ability to absorb calcium, decreased levels of sex hormones, especially estrogen and androgen, and a negative calcium balance.

Similar symptoms of bone loss characterize senile osteoporosis and steroid-induced osteoporosis, the latter being a recognized result of long term glucocorticoid (cortico-steroid) therapy for certain disease states.

Methods of treating osteoporosis have varied considerably but to date no totally satisfactory treatment is yet known. A conventional treatment is to administer a calcium supplement to the patient. However, calcium supplementation by itself has not been successful in preventing or curing the disease. Another conventional treatment is the injection of sex hormones, especially estrogen, which has been reported to be effective in preventing the rapid loss of bone mass experienced in postmenopausal women. This technique, however, has been complicated by the fear of its possible carcinogenicity. Other treatments for which variable results have been reported, have included a combination of vitamin D in large doses, calcium and fluoride. The primary problem with this approach is that fluoride induces structurally unsound bone, called woven bone, and in addition, produces a number of side effects such as increased incidence of fractures and gastrointestinal reaction to the large amounts of fluoride administered. Another suggested method is to block bone resorption by injecting calcitonin or providing phosphonates.

U.S. Pat. No. 4,255,596 suggests the use of various metabolites of vitamin $D_3$ for increasing calcium absorption and retention within the body of mammals displaying evidence of or having a physiological tendency toward loss of bone mass. The metabolites specifically named in that patent, i.e., 1α-hydroxyvitamin $D_3$, 1α-hydroxyvitamin $D_2$, 1α,25-dihydroxyvitamin $D_3$ (calcitriol), 1α,25-dihydroxyvitamin $D_2$ and 1,24,25-trihydroxyvitamin $D_3$, although capable of the activity described and claimed in that patent, can, however, also cause hypercalcemia, especially if used with the conventional calcium supplement. Calcitriol treatment has also been found to be effective in reducing bone loss in women with postmenopausal osteoporosis by increasing intestinal calcium absorption and reducing bone resorption. Aloria et al, "Calcitriol In The Treatment Of Postmenopausal Osteoporosis", Amer. Jour. of Med., Vol. 84, March, 1988, pp. 401–408. Again, however, Aloria et al discouraged the use of oral dosages of calcitriol due to the risk of hypercalcemia. Therefore, use of calcitriol to treat osteoporosis has not been widely accepted.

Another important consideration is that in vivo calcitriol is produced slowly and continuously by the kidney and thus is available throughout the day and night. When given by mouth or by injection, large amounts are available to the tissues initially but little is left after 2–4 hours due to metabolism and excretions. A process whereby calcitriol can be made available in vivo more slowly and more continuously would avoid peaks and valleys in the availability of calcitriol thereby providing an effective in vivo level of the compound over a more prolonged period of time and also avoiding or substantially reducing episodes of hypercalcemia that often result from the sudden availability of excessive amounts of the substance.

SUMMARY OF THE INVENTION

The present invention provides a method for modulating and regulating the in vivo activity of biologically active vitamin D compounds, such as calcitriol or analogs of calcitriol. More specifically, this invention provides modified vitamin D compounds that exhibit a desirable and highly advantageous pattern of biological acitivity in vivo, namely, the more gradual onset and more prolonged duration of activity. As a consequence of such advantageous properties, these compounds represent novel therapeutic agents for the treatment of all diseases where vitamin D compounds have been shown effective, such as metabolic bone diseases or proliferative skin disorders (e.g. psoriasis)

and they should prove especially useful for the treatment of diseases where bone formation is desired, such as osteoporosis (postmenopausal, senile, or steroid-induced), osteomalacia or renal osteodystrophy.

Structurally, the key feature of the modified vitamin D compounds having these desirable biological attributes is that they are derivatives of 1α,25-dihydroxyvitamin $D_3$, or derivatives of 1α,25-dihydroxyvitamin $D_3$ analogs, in which a hydrolyzable group is attached to the hydroxy group at carbon 25 and, optionally, to any other of the hydroxy groups present in the molecule. Depending on various structural factors—e.g. the type, size, structural complexity—of the attached group, these derivatives are thought to hydrolyze to 1α,25-dihydroxyvitamin $D_3$, or to a 1α,25-dihydroxyvitamin $D_3$ analog, at different rates in vivo, thus providing for the "slow release" of the biologically active vitamin D compound (i.e. 1,25-dihydroxyvitamin $D_3$, or an analog thereof) in the body.

The "slow release" in vivo activity profiles of such compounds can, of course, be further modulated by the use of mixtures of derivatives (e.g. mixtures of different derivatives of 1,25-dihydroxyvitamin $D_3$, or different derivatives of 1,25-dihydroxyvitamin $D_3$ analogs) or the use of mixtures consisting of one or more vitamin D derivative together with underivatized vitamin D compounds.

It is important to stress that the critical structural feature of the vitamin derivatives identified above is the presence of a hydrolyzable group attached to the hydroxy group at carbon 25 of the molecule. The presence of a hydrolyzable group at that position imparts on the resulting derivatives the desirable "slow-release" biological activity profile mentioned above. Other hydroxy functions occurring in the molecule (e.g. hydroxy functions at carbons 1 or 3) may be present as free hydroxy groups, or one or more of them may also be derivatived with a hydrolyzable group. The fact that the introduction of a hydrolyzable group at carbon 25 of the vitamin D molecule markedly modulates the in vivo biological activity pattern of the resulting derivative was not appreciated previously. The realization of the importance of this specific modification, and the demonstration of its marked and highly beneficial biological effects form the basis of this invention.

The "hydrolyzable group" present in the above-mentioned derivatives is preferably an acyl group, i.e. a group of the type $Q^1CO$—, where $Q^1$ represents hydrogen or a hydrocarbon radical of from 1 to 18 carbons that may be straight chain, cyclic, branched, saturated or unsaturated. Thus, for example, the hydrocarbon radical may be a straight chain or branched alkyl group, or a straight chain or branched alkenyl group with one or more double bonds, or it may be an optionally substituted cycloalkyl or cycloalkenyl group, or an aromatic group, such as substituted or unsubstituted phenyl, benzyl or naphthyl. Especially preferred acyl groups are alkanoyl or alkenoyl groups, of which some typical examples are formyl, acetyl, propanoyl, hexanoyl, isobutyryl, 2-butenoyl, palmitoyl or oleoyl. Another suitable type of hydrolyzable group is the hydrocarbyloxycarbonyl group, i.e. a group of the type $Q^2$—O—CO—, where $Q^2$ is a $C_1$ to $C_{18}$ hydrocarbon radical as defined above. Exemplary of such hydrocarbon radicals are methyl, ethyl, propyl, and higher straight chain or branched alkyl and alkenyl radicals, as well as aromatic hydrocarbon radicals such as phenyl or benzoyl.

Among the modified vitamin D compounds having the desirable in vivo bioactivity profile indicated above, an especially important and preferred class are certain acyl ester derivatives of calcitriol, i.e. the calcitriol derivatives characterized by the following general structure:

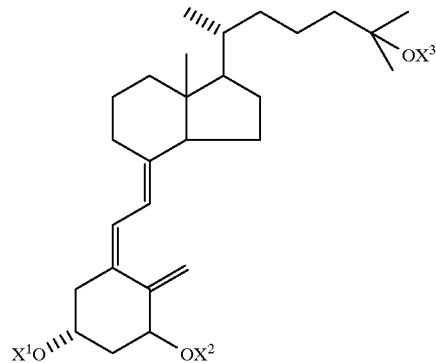

where $X^1$ and $X^2$, independently represent hydrogen or an acyl group, and where $X^3$ represents an acyl group as previously defined. Two other very important groups of modified vitamin D compounds are the corresponding acyl esters of the calcitriol side chain homologs, and the acyl derivatives of the 19-nor-1,25-dihydroxyvitamin D analogs.

The present invention, therefore, provides a series of modified vitamin D compounds that are useful for the treatment of metabolic bone disease (such as the various forms of osteoporosis, osteomalacia, osteodystrophy, etc.) or of differentiative diseases such as psoriasis or malignancies. More specifically, a method of treating such diseases comprises the administration of an effective amount of the above-indicated acyl ester derivatives of 1α,25-dihydroxyvitamin $D_3$ or of the corresponding derivatives of 1α,25-dihydroxyvitamin $D_3$ analogs.

The above compounds may be administered alone or in combination with other pharmaceutically acceptable agents. Dosages of from not less than about 0.5 μg per day to not more than about 10 μg per day of the individual compound per se, or in combinations, are generally effective. This method has the distinct advantage that it will restore bone mass due to the conversion of these compounds to calcitriol which has been proven to be effective in the treatment of osteoporosis. Further, these compounds advantageously will be less likely to cause hypercalcemia or hypocalcemia then the underivatized compounds even if the compound is administered continuously on a daily basis, as long as the appropriate compounds and dosages are used, it being understood that the compounds and the dosage levels will be adjusted dependent upon the response of the subject as monitored by methods known to those skilled in the art.

The above method, involving the administration of the indicated dosages of these compounds is effective in restoring or maintaining bone mass, and thus provides a novel method for the treatment or prevention of various forms of osteoporosis such as postmenopausal osteoporosis, senile osteoporosis and steroid-induced osteoporosis. It will be evident that the method will find ready application for the prevention or treatment of disease states other than those named, in which the loss of bone mass is an indication. Also, it will be further evident that the method will find ready application for the prevention or treatment of hypercalcemia and hypocalcemia as the rate of conversion of these analogs, i.e. the in vivo hydroxylation process, can be controlled and regulated in the manner described above.

DISCLOSURE OF THE INVENTION

Figure 1:
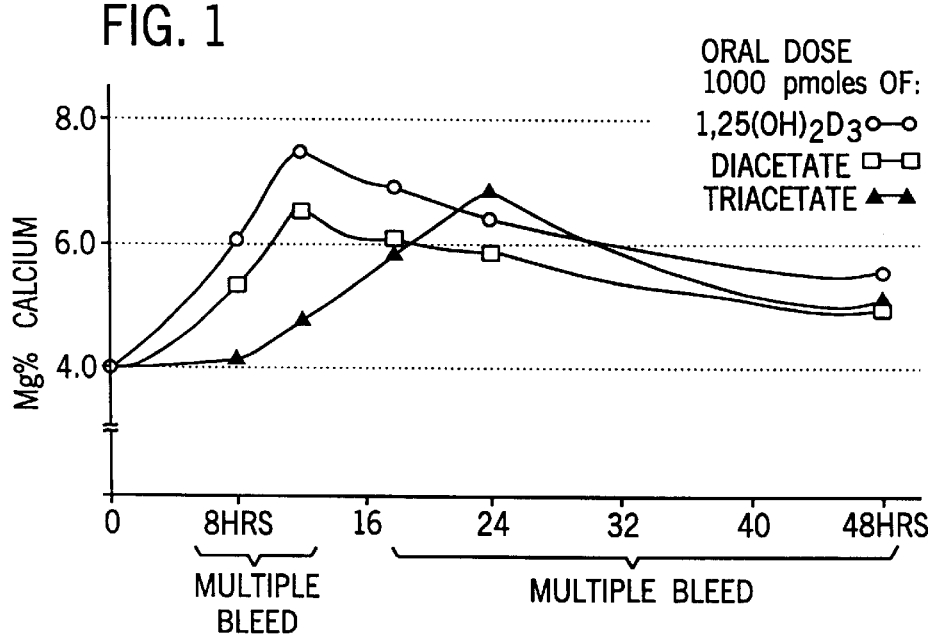
FIG. 1 is a graph illustrating the activity of di- and tri-acetates of 1α,25-dihydroxyvitamin $D_3$ on serum calcium, and particularly illustrates the milligrams percent calcium found in blood over time.

The present invention provides novel modified vitamin D compounds which are useful in the treatment of metabolic bone diseases, such as osteoporosis, as well as other disease states. These modified vitamin D compounds are hydrolyzable in vivo to calcitriol, or analogs of calcitriol, over a period of time following administration, and as a consequence regulate the in vivo availability of active calcitriol, or analogs of calcitriol, thereby also modulating their activity profile in vivo. The term "activity profile" refers to the biological response over time of vitamin D compounds such as calcitriol or analogs of calcitriol. Individual modified compounds, or mixtures of such compounds, can be administered to "fine tune" a desired time course of response.

As used herein the term "vitamin D compound" encompasses compounds which have the C-ring, D-ring and 3β-hydroxycyclohexane A-ring of vitamin D interconnected by the 5,7 diene double bond system of vitamin D together with any side chain attached to the D-ring. In other words, the vitamin D compounds encompassed herein include those having a "vitamin D nucleus" comprising substituted or unsubstituted A-, C-, and D-rings interconnected by a 5, 7 diene double bond system typical of vitamin D together with a side chain attached to the D-ring. As used herein the term "modified vitamin D compound" encompasses any vitamin D compound in which one or more of the hydroxy functions present in such a compound are modified by derivatization with a hydrolyzable group. A "hydrolyzable group" is a hydroxy-modifying group that can be hydrolyzed in vivo, so as to regenerate the free hydroxy functions.

In the context of this disclosure, the term hydrolyzable group preferably includes acyl and hydrocarbyloxycarbonyl groups, i.e. groups of the type $Q^1CO$— and $Q^2$—O—CO, respectively, where $Q^1$ and $Q^2$ have the meaning defined earlier.

Structurally, the modified vitamin D compounds encompassed may be represented by the formula:

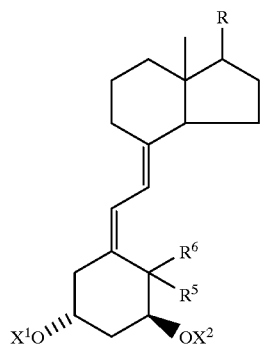

where $R^5$ and $R^6$ each represent hydrogen, or taken together $R^5$ and $R^6$ represent a methylene group.

The side chain group R in the above-shown structure represents a steroid side chain of the structure below:

where the stereochemical center (corresponding to C-20 in steroid numbering) may have the R or S configuration, (i.e. either the natural configuration about carbon 20 or the opposite unnatural configuration), and where Z is selected from Y, —OY, —$CH_2OY$, —C≡CY and —CH═CHY, where the double bond may have the cis or trans geometry, and where Y is selected from a radical of the structure:

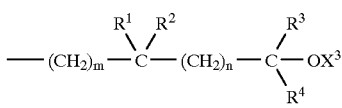

where m and n, independently, represent the integers from 0 to 5, where $R^1$ is selected from hydrogen, $OX^4$, fluoro, trifluoromethyl, and $C_{1-5}$-alkyl, which may be straight chain or branched and, optionally, bear a hydroxy substituent, and where $R^2$ is selected from hydrogen, fluoro, trifluoromethyl and $C_{1-5}$ alkyl, which may be straight-chain or branched, and optionally, bear a hydroxy substituent, and where $R^3$ and $R^4$, independently represent trifluoromethyl or $C_{1-5}$ alkyl, which may be straight chain or branched and, optionally, bear a hydroxy substituent, and where $R^1$ and $R^2$, taken together, represent an oxo group, or an alkylidene group, ═$CR^2R^2$, or ═$CR^2R^3$, or the group —$(CH_2)_p$—, where p is an integer from 2 to 5, and where $R_3$ and $R_4$, taken together, represent the group —$(CH_2)_q$—, where q is an integer from 2 to 5. In the above-shown structures $X^1$, $X^2$ and $X^4$ independently represent hydrogen, an acyl group or a hydrocarbyloxycarbonyl group, and $X^3$ represents an acyl group or a hydrocarbyloxycarbonyl group, as previously defined herein.

Some specific examples of such modified vitamin D compounds include calcitriol derivatives such as:

1α,25(OH)$_2$-D$_3$-1,3,25-Triacetate where $X^1$═$X^2$═$X^3$═$CH_3CO$;

1α,25(OH)$_2$-D$_3$-1,3,25-Trihexanoate where $X^1$═$X^2$═$X^3$═$CH_3(CH_2)_4CO$;

1α,25(OH)$_2$-D$_3$-1,3,25-Trinonanoate where $X^1$═$X^2$═$X^3$═$CH_3(CH_2)_7CO$;

1α,25(OH)$_2$-D$_3$-25-Acetate where $X^1$═$X^2$═H and $X^3$═$CH_3CO$.

The following examples, which are meant to be illustrative only, describe the process of synthesis of modified vitamin D compounds. In these examples, specific compounds identified by Arabic numerals (e.g. compounds 1, 2, 3, . . . etc.) refer to the structures so numbered below. Additionally, examples are provided which are illustrative of the distinctive biological characteristics of the new compounds, such characteristics serving as a basis for the application of these compounds in the treatment of metabolic bone disease and other vitamin D responsive diseases such as psoriasis.

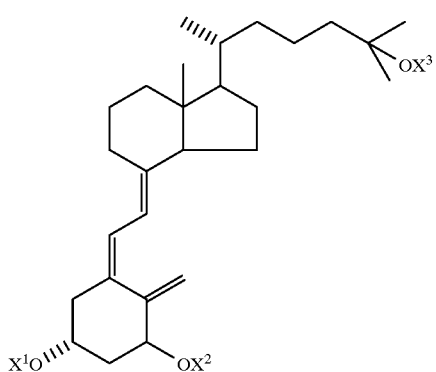

1: $X^1=X^2=X^3=H$
2: $X^1=X^2=X^3=CH_3CO$
3: $X^1=X^2=X^3=CH_3(CH_2)_4CO$
4: $X^1=X^2=X^3=CH_3(CH_2)_7CO$
5: $X^1=X^2=(CH_3)_2CHCO; X^3=H$
6: $X^1=X^2=CH_3(CH_2)_4CO; X^3=H$
7: $X^1=X^2=C_6H_5CO; X^3=H$
8: $X^1=X^2=H; X^3=CH_3CO$

EXAMPLE 1

The Preparation of Mono, Di and Tri-Esters of $1\alpha,25$-$(OH)_2$-$D_3$

Experimental

Spectra were obtained on the following instruments: Ultraviolet (UV) absorption spectra were taken with Perkin-Elmer Lambda 3B UV/vis spectrophotometer. Nuclear magnetic resonance (NMR) spectra were recorded at 400 or 500 MHz with a Bruker DMX spectrometer. Chemical shifts ($\delta$) are reported downfield from internal $Me_4Si$ ($\delta 0.00$). Mass spectra were recorded at 70 eV on a Kratos MS-50 TC instrument equipped with a Kratos DS-55 data system. Preparative thin layer chromatography (p.l.c.) was carried out with Merk 1-mm F-254 silica gel plates and E. Merk 0.25 mm F-254 silica gel plates.

General Procedure for Preparation of Triesters: Preparation of $1\alpha,25(OH)_2$-$D_3$ 1,3,25-Triacetate (2) $X^1=X^2=X^3=CH_3CO$. A solution of glacial acetic acid (0.05 mL, 0.87 mmol). trifluoroacetic anhydride (0.05 mL, 0.35 mmol) was stirred at room temperature 3.5 h. Then $1\alpha,25(OH)_2$-$D_3$ (1) (0.3 mg, 0.00072 mmol) in 0.4 mL dry THF was added to above solution at 0° C. The reaction mixture was stirred at 0° C. for 0.5 h and then at room temperature for 2 h. The solvent was removed under reduced pressure to afford a crude product that was purified twice by preparative thin layer chromatography (p.l.c., 15% EtOAc/hexane) to give a pure compound (2) (0.122 mg, 31.3% yield). UV, $\lambda$ max 265 nm (Et OH). $^1$H NMR ($CDCl_3$): $\delta$, 0.51 (s, 3H, $C_{18}$—$CH_3$), 0.92(d, J=5.0 Hz, 3H, $C_{21}$—$CH_3$), 1.42 (s, 6H, $C_{26,27}$—$CH_3$), 1.98, 2.04, 2.06 (s, 9H, $CH_3CO$—), 5.04 (s, 1H, $C_{19}$ E-H), 5.18 (m, 1H, $C_3$—H), 5.31 (s, 1H, $C_{19}$ Z-H), 5.48 (t, J=6 Hz, $C_1$—H), 5.91 (6.35 (dd, J=10 Hz, $C_{6,7}$—H), MS: m/z 542 ($M^+$) 482 ($M^+$-60), 422 ($M^+$-2 x 60), 362 ($M^+$3 x 60).

$1\alpha,25$ $(OH)_2$-$D_3$ 1,3,25-Trihexanoate (3) $X^1=X^2=X^3=CH_3(CH_2)_4$ CO. To hexanoic acid (0.15 mL, 1.20 mmol) was added trifluoroacetic anhydride (0.1 mL 0.71 mmol). The mixture was stirred at room temperature for 4 h (the solution became pale brow n). After $1\alpha,25(OH)_2$-$D_3$ (1) (0.4 mg, 0.00096 mmol) in 0.2 mL dry THF was added, the reaction mixture was stirred at room temperature for 5 h, or until complete (as monitored by thin layer chromotography). The product (3) (0.217 mg, 31.72% yield) was worked-up as in the previous example and purified by p.l.c. (3 times; 8% EtOAc/Skellysolve B). UV, $\lambda$ max 265.3 nm, 245 nm (shoulder) (EtOH). $^1$H NMR ($CDCl_3$): $\delta$, 0.51, (s, 3H, $C_{18}$—$CH_3$), 0.89 (t, J=6.3 Hz, 9H, $CH_3(CH_2)_4$ CO), 0.92 (d, J=6.3 Hz, 3H, $C_{21}$—$CH_3$), 1.42 (s, 6H, $C_{26,27}$—$CH_3$), 5.14 (s, 1H, $C_{19}$ E-H), 5.18 (m, 1H, $C_3$—H), 5.32 (s, 1H, $C_{19}$ Z-H), 5.47 (t, J=6.3 Hz, 1H, $C_1$—H), 5.91, 6.34 (dd, J=11.15 Hz $C_{6,7}$—H), MS: m/z 710 ($M^+$), 594 ($M^+$-116 $C_5H_{11}COOH$), 478 ($M^+$-2 x 116), 362 ($M^+$-3 x 116).

$1\alpha,25(OH)_2$-$D_3$ 1,3,25-Trinonanoate (4) $X^1=X^2=X^3=CH_3(CH_2)_7CO$. To nonanoic acid (0.2 mL, 1.145 mmol) was added trifluoroacetic anhydride (0.08 mL, 0.566 mmol), and the mixture was stirred at room temperature for 4 h. After $1\alpha,25(OH)_2$-$D_3$ (1) (0.4 mg, 0.00096 mmol) in dry THF (0.2 mL) was added, the reaction mixture was stirred at room temperature for 4 h, or until complete (as determined by TLC). The usual work-up gave product (4) (0.283 mg, 35.2% yield). UV, $\lambda$ max 265.3 nm 243.9 nm (shoulder) (EtOH); $^1$H NMR ($CDCl_3$): $\delta$, 0.51 (s, 3H, $C_{18}$—$CH_3$), 0.88 (t, J=6.2 Hz, 9H, $CH_3$ $(CH_2)_7CO$—), 0.92 (d, J=6.3 Hz, 3H, $C_{21}$—$CH_3$), 1.42 (s, 6H, $C_{26,27}$—$CH_3$), 5.04 (s, 1H, $C_{19}$ E-H), 5.18 (m. 1H, $C_3$—H), 5.32 (s, 1H, $C_{19}$ Z-H), 5.49 (t, J=6.2 Hz, 1H, $C_1$—H), 5.91, 6.34 (dd, J=11.36 Hz, 2H, $C_{6,7}$—H). MS: m/z 836 ($M^+$), 678 ($M^+$-158, $CH_3$ $(CH_2)_7COOH$), 520 ($M^+$-2 x 158), 362 ($M^+$-3 x 158).

General Procedure for Preparation of Diesters: Preparation of $1\alpha,25(OH)_2$-$D_3$ 1,3-diisobutyrate (5) $X^1=X^2=(CH_3)_2CHCO; X^3=H$; A solution of isobutyric acid (0.06 mL, 0.647 mmol), N,N-dicyclohexylcarbodimide (35.55 mg, 0.173 mmol), 4-pyrrolidinopyridine (6.12 mg, 0.041 mmol) and $1\alpha,25(OH)_2$-$D_3$ (1) (0.4 mg, 0.00096 mmol) in 0.15 mL dry dichloromethane was stirred at room temperature overnight (12 h). The white precipitate formed was filtered and the residue washed with dichloromethane. The combined organic solution was concentrated and the crude product was purified twice by p.l.c. (25% EtOAc/skellysove B) to give a pure product (5) (296 mg, 55.33% yield). UV, $\lambda$ max 266.5 nm, 244 nm (shoulder); $^1$H NMR ($CDCl_3$): $\delta$, 0.49 (s, 3H, $C_{18}$—$CH_3$), 0.93 (d, J=6.25 Hz, 3H, $C_{21}$—$CH_3$), 1.14 (t, J=6.3 Hz, 12H, $(CH_3)_2CHCO$—), 1.21 (s, 6H, $C_{26,27}$—$CH_3$), 5.05 (s, $C_{19}$ E-H), 5.17 (m, 1H, $C_3$—H), 5.35 (s, 1H, C19 Z-H). 5.5 (t, J=6.3 Hz, 1H, $C_1$—H), 5.91, 6.35 (dd, J=11.35 Hz, 2H, $C_{6,7}$—H) MS: m/z 556 ($M^+$), 468 ($M^+$-88,$(CH_3)_2CHCOOH$), 380 ($M^+$-2 x 88), 362 ($M^+$-2 x 88-$H_2O$).

$1\alpha,25(OH)_2$-$D_3$ 1,3-Dihexanoate (6), $X^1=X^2=CH_3$ $(CH_2)_4CO$, $X^3=H$. A solution of n-hexanoic acid (0.15 mL, 1.19 mmol), N,N-dicyclohexylcarbodimide (73.66 mg, 0.358 mmol), 4-pyrrolidinopyridine (4.45 mg, 0.03 mmol), and $1\alpha,25(OH)_2$-$D_3$ (1) (0.5 mg, 0.0012 mmol) in 0.1 mL dry dichloromethane was stirred at room temperature overnight (12 h) After work-up as in the preceding example, the crude product was purified by p.l.c. (3 times, 15% EtOAc/skellysolve B) to give pure compound (6) (0.079 mg, 10.74% yield). UV, $\lambda$ max 263.6 nm, 240 nm (EtOH). $^1$H NMR ($CDCl_3$): $\delta$, 0.51 (s, 3H, $C_{18}$—$CH_3$), 0.89 (t, J=6.4 Hz, 6H, $CH_3(CH_2)_4CO$—), 0.93 (d, J=6.25 Hz, 3H, $C_{21}$—$CH_3$), 1.21 (s, 6H, $C_{26,27}$—$CH_3$), 5.04 (s, 1H, $C_{19}$ E-H), 5.18 (m, 1H, $C_3$—H), 5.30 (s, 1H, $C_{19}$ Z-H), 5.49 (t, J=6.2 Hz, 1H, $C_1$—H), 5.92, 6.34 (dd, J=11.26 Hz, 2H, C6,7—H). MS: m/z 612 ($M^+$), 496 ($M^+$-116, $CH_3(CH_2)_4COOH$), 478 ($M^+$-116-$H_2O$), 380 ($M^+$-2 x 116), 362 ($M^+$-2 x 116-$H_2O$).

$1\alpha,25(OH)_2D_3$ 1,3-Dibenzoate (7) $X^1=X^2=C_6H_5CO$, $X^3=H$. A solution of benzoic acid (15.53 mg, 0.127 mmol), N,N-dicyclohexylcarbodimide (42.64 mg, 0.206 mmol), 4-pyrrolidinopyridine (2.13 mg, 0.0144 mmol), and $1\alpha,25$ $(OH)_2D_3$ (1) (0.51 mg, 0.00123 mmol) in dry dichloromethane (0.4 mL) was stirred at room temperature for 16 h. After work-up as above, the crude product was purified by p.l.c. (2 times, 8% EtOAc/skellysolve B) to give a pure compound (7) (0.123 mg, 16.4% yield). UV, $\lambda$ max 265.4 nm, 230.5 nm (EtOH), $^1$H NMR ($CDCl_3$) $\delta$, 0.28 (s, 3H, $C_{18}$—$CH_3$), 0.91 (d, J=5.0 Hz, $C_{21}$—$CH_3$), 1.21 (s, 6H, $C_{26,27}$—$CH_3$), 5.13 (s, 1H, $C_{19}$ E-H), 5.47 (s, 1H, $C_{19}$ Z-H), 5.51 (m, 1H, $C_3$—H), 5.82 (t, J=6.2 Hz, 1H, $C_1$—H), 5.93, 6.45 (dd, J=10, $C_{6,7}$—H), 7.41, 7.54, 8.04 (m, 10H, Ar—H). MS: m/z 624 ($M^+$), 606 ($M^+$-$H_2O$), 502 ($M^+$-122 $C_6H_5COOH$), 380 ($M^+$-2 x 122), 362 ($M^+$-2 x 122-$H_2O$).

$1\alpha,25(OH)_2$-$D_3$ 25-Acetate (8) $X^1=X^2=H$, $X^3=CH_3CO$. $1\alpha,25(OH)_2$-$D_3$ 1,3,25-Triacetate (2) (0.168 mg, 0.00031 mmol) was dissolved in 1 mL of 0.6% methanolic solution of potassium carbonate. After the mixture was stirred at room temperature for 2 h (or until complete by TLC), the solvent was removed under reduced pressure. The crude product was purified by p.l.c. (50% EtOAc/hexane) to give the pure product (8) (0.056 mg, 39.4% yield). UV, $\lambda$ max 265 nm (EtOH), $^1$H NMR ($CDCl_3$); $\delta$, 0.54 (s, 3H, $C_{18}$—$CH_3$), 0.92 (d, J=5 Hz, $C_{21}$—$CH_3$), 1.42 (s, 6H, $C_{26,27}$—$CH_3$), 1.98 (s, 3H, $CH_3CO$), 4.24 (m, 1H, $C_3$—H), 4.44 (t, J=6 Hz, $C_1$—H), 5.01 (s, 1H, $C_{19}$ E-H), 5.34 (s, 1H, $C_{19}$ Z-H), 6.02, 6.39 (dd, J=10 Hz, 2H, $C_{6,7}$—H), MS: m/z 458 ($M^+$), 440 ($M^+$-$H_2O$), 422 ($M^+$-2 x $H_2O$), 398 ($M^+$-60, $CH_3COOH$), 380 ($M^+$-60-$H_2O$), 362 ($M^+$-60-2 x $H_2O$).

EXAMPLE 2

This example illustrates the serum calcium response of rats over time to three compounds, namely, $1\alpha,25(OH)_2D_3$-1,3,25-triacetate, $1\alpha,25(OH)_2D_3$-1,3-diacetate, and $1\alpha,25(OH)_2D_3$ (unesterified).

In this biological test, rats were fed a calcium-containing (0.47% calcium), vitamin D-deficient diet for a period of 8 weeks to deplete them of vitamin D. They were then provided a single oral dose of 1,000 pmol or 1 nanomole of each of the compounds, and serum calcium was determined by bleeding the rats at the various times as shown in Table 1. FIG. 1 is a graph illustrating the data of Table 1. Because calcium is present in the diet and hence their intestine, the rise in serum calcium largely represents intestinal calcium absorption. The results show clearly that the 1,3-diacetate and un-esterified calcitriol produce essentially the same time course of response, illustrating that acetylation of the C-1 and C-5 hydroxy groups does not significantly alter the biological response, presumably because the acyl groups at these positions are removed rapidly, e.g. by digestive enzymes. In marked contrast, the triacetate did not begin to show a response until 12 to 18 hours post-dose, peaking at 24 hours. Thus, the 25-acetate group probably remained intact over a more prolonged period and was then slowly hydrolyzed inside the body. Thus, the triacetate clearly delays utilization of the calcitriol indicating that the in vivo activity profile of the parent calcitriol can be changed very markedly by acylation of the C-25-hydroxy group.

TABLE 1

| Time | Control | (A) $1.25(OH)_2D_3$ | (B) Diacetate | (C) Triacetate |
|---|---|---|---|---|
| 0 Hours | 4.3 ± 0.07 | | | |
| 8 Hours | | 6.06 ± 0.89 | 5.42 ± 0.90 | 4.06 ± 0.38 |
| 12 Hours | | 7.39 ± 0.10 | 6.50 ± 0.13 | 4.70 ± 0.12 |
| 18 Hours | | 6.97 ± 0.51 | 6.24 ± 0.51 | 5.91 ± 0.30 |
| 24 Hours | | 6.45 ± 0.50 | 5.98 ± 0.43 | 6.7 ± 0.54 |
| 48 Hours | 4.43 ± 0.18 | 5.59 ± 0.80 | 5.11 ± 0.48 | 5.10 ± 0.43 |

All data = Mean ± S.D.
(A) from (B), N.S. diff.
(A) from (C), at 8 hrs, 12 hrs, p < 0.001

EXAMPLE 3

This example illustrates the serum calcium response of rats over time to two compounds, namely, $1\alpha,25(OH)_2D_3$ (unesterified) and $1\alpha,25(OH)_2D_3$-25-acetate, administered by three different methods, namely, orally (oral), intramuscularly (I.M.), and subcutaneously (Sub. Cu.).

Figure 2:
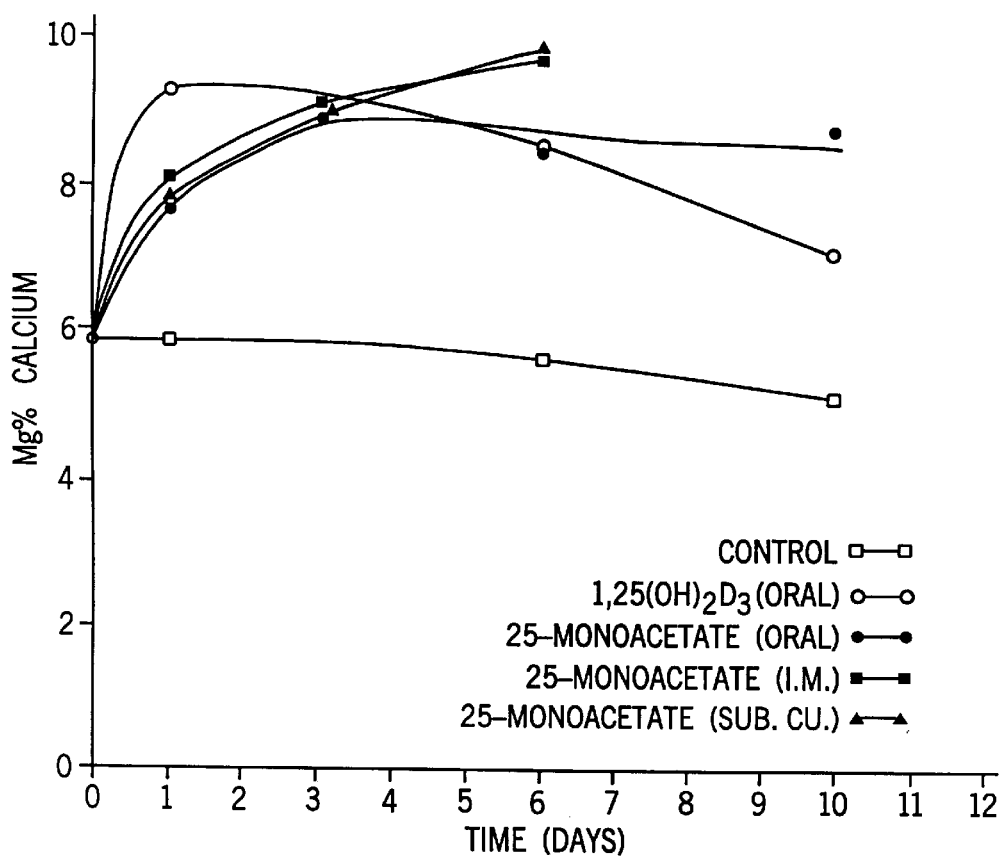
FIG. 2 is a graph similar to FIG. 1 except illustrating the activity of a 25-mono-acetate of 1α,25-dihydroxyvitamin $D_3$ on serum calcium.

In this test, 1 nanomole of each compound was given to vitamin D deficient rats fed a 0.47% calcium, 0.3% P diet in 0.1 ml propylene glycol 95%/5% ethanol. There were at least 4 rats per group. Serum calcium was determined at the various times shown in Table 2 following a single dose given by the indicated route. FIG. 2 is a graph illustrating the data of Table 2. The results are in accord with those of Example 2. Regardless of route of administration $1,25(OH)_2D_3$-25-acetate shows a more gradual onset of in vivo activity and a delayed peak of activity. Thus, the 25-monoacetate clearly delays utilization of the calcitriol confirming that the presence of a C-25-O-acyl group has a pronounced effect on the activity pattern and time course of response of a biologically active vitamin D compound.

TABLE 2

Serum Calcium Response to $1,25$-$(OH)_2D_3$ and its 25-Acetate

| Compound | Administration Route | Serum Calcium (mg/100 ml) | | | |
|---|---|---|---|---|---|
| | | Day 1 | Day 3 | Day 6 | Day 10 |
| None (Control) | | 5.9 ± 0.34 | — | 5.7 ± 0.34 | 5.2 ± 0.63 |
| 1,25-$(OH)_2D_3$ | Oral | 9.33 ± 0.41 | — | 8.6 ± 0.52 | 7.15 ± 0.68 |
| 1,25-$(OH)_2D_3$ 25-Acetate | Oral | 7.70 ± 0.11 | 8.87 ± 0.6 | 8.54 ± 0.15 | 8.83 ± 0.71 |
| 1,25-$(OH)_2D_3$ 25-Acetate | I.M. | 8.10 ± 0.24 | 9.17 ± 0.53 | 9.77 ± 0.3 | — |
| 1,25-$(OH)_2D_3$ 25-Acetate | Sub. Cu. | 7.78 ± 0.28 | 9.00 ± 0.28 | 9.84 ± 0.39 | — |

The modified vitamin D compound or combinations thereof can be readily administered as sterile parenteral solutions by injection or intravenously, or by alimentary canal in the form of oral dosages, or trans-dermally, or by suppository. Doses of from about 0.5 micrograms to about 10 micrograms per day or modified vitamin D compound per se, or in combination with other modified vitamin D compounds, the proportions of each of the compounds in the combination being dependent upon the particular disease state being addressed and the degree of bone mineralization and/or bone mobilization desired, are generally effective to practice the present invention. In all cases sufficient amounts of the compound should be used to restore bone mass. Amounts in excess of about 10 micrograms per day of modified vitamin D compound, or the combination of that compound with other modified vitamin D compounds, are generally unnecessary to achieve the desired results, may result in hypercalcemia, and may not be an economically sound practice. In practice the higher doses are used where therapeutic treatment of a disease state is the desired end while the lower doses are generally used for prophylactic purposes, it being understood that the specific dosage administered in any given case will be adjusted in accordance with the specific compounds being administered, the disease to be treated, the condition of the subject and the other relevant medical facts that may modify the activity of the drug or the response of the subject, as is well known by those skilled in the art. In general, either a single daily dose or divided daily dosages may be employed, as is well known in the art.

Dosage forms of the various compounds can be prepared by combining them with non-toxic pharmaceutically acceptable carriers to make either immediate release or slow release formulations, as is well known in the art. Such carriers may be either solid or liquid such as, for example, corn starch, lactose, sucrose, peanut oil, olive oil, sesame oil and propylene glycol. If a solid carrier is used, the dosage form of the compounds may be tablets, capsules, powders, troches or lozenges. If a liquid carrier is used, soft gelatin capsules, or syrup or liquid suspensions, emulsions or solutions may be the dosage form. The dosage form may also contain adjuvants, such as preserving, stabilizing, wetting or emulsifying agents, solution promoters, etc. They may also contain other therapeutically valuable substances.

We claim:

1. A method of treating a disease in a patient in need of prolonged treatment and that responds to an active vitamin D compound, comprising selecting an active vitamin D compound having a hydroxy group at carbon 25 and having a desirable in vivo therapeutic activity for treating the disease;

prolonging the duration of the in vivo therapeutic activity of said active vitamin D compound by providing a derivatized form of said active vitamin D compound, said derivatized vitamin D compound having a group —$OX^3$ at carbon 25 where $X^3$ is an in vivo hydrolyzable group; and administering an effective dose of said derivatized vitamin D compound to a subject in need thereof.

2. The method of claim 1 wherein said derivatized vitamin D compound has the formula:

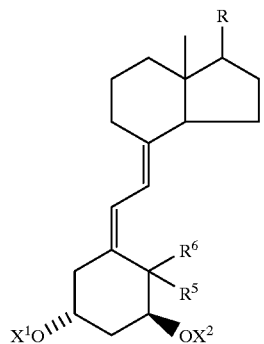

where $R^5$ and $R^6$ each represent hydrogen, or taken together $R^5$ and $R^6$ represent a methylene group, and where R is represented by the structure:

where the stereochemical center at carbon 20 in the side chain may have the R or S configuration, and where Z is selected from Y, —OY, —$CH_2OY$, —C≡CY and —CH═CHY, where the double bond may have the cis or trans stereochemical configuration, and where Y is selected from a radical of the structure:

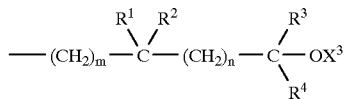

where m and n, independently, represent the integers from 0 to 5, where $R^1$ is selected from the group consisting of hydrogen, $OX^4$, fluoro, trifluoromethyl, and $C_{1-5}$-alkyl which may be straight chain or branched and, optionally, bear a hydroxy substituent, and where $R^2$ is selected from the group consisting of hydrogen, fluoro, trifluoromethyl and $C_{1-5}$ alkyl, which may be straight-chain or branched, and optionally, bear a hydroxy substituent, and where each of $R^3$ and $R^4$, is selected from trifluoromethyl and $C_{1-5}$ alkyl, which may be straight chain or branched and optionally bear a hydroxy substituent, and where $R^1$ and $R^2$, taken together, represent an oxo group, or an alkylidene group, ═$CR^2R^2$, ═$CR^2R^3$, or the group —$(CH_2)_p$—, where p is an integer from 2 to 5, and where $R_3$ and $R_4$, taken together, represent the group —$(CH_2)_q$—, where q is an integer from 2 to 5, and where $X^1$, $X^2$, and $X^4$ are each hydrogen, an acyl group, or a hydrocarbyloxycarbonyl group, and where $X^3$ represents an acyl group or a hydrocarbyloxycarbonyl group.

3. The method of claim 2 wherein the acyl group is selected from the group consisting of acetyl, propanoyl, butanoyl and hexanoyl.

4. The method of claim 1 wherein said derivatized compound is combined with a non-toxic pharmaceutically acceptable carrier and is administered in liquid form.

5. The method of claim 4 wherein said derivatized compound is administered by injection.

6. The method of claim 4 wherein said derivatized compound is administered intravenously.

7. The method of claim 4 wherein said derivatized compound is administered orally.

8. The method of claim 1 wherein said derivatized compound is combined with a non-toxic pharmaceutically acceptable carrier and is administered in solid form.

9. The method of claim 8 wherein said derivatized compound is administered by suppository.

10. The method of claim 8 wherein said derivatized compound is administered topically.

11. The method of claim 8 wherein said derivatized compound is administered orally.

12. The method of claim 1 wherein said disease is selected from the group consisting of renal osteodystrophy, hypoparathyroidism, pseudohypoparathyroidism, hypocalcemia, osteomalacia, vitamin D-deficient rickets, postmenopausal osteoporosis, estrogen-lack osteoporosis, senile osteoporosis, steroid-induced osteoporosis, and psoriasis.

13. The method of claim 1 wherein said derivatized vitamin D compound is administered in an amount from about 0.5 μg/day to about 10 μg/day.

14. The method of claim 1 wherein at least two derivatized vitamin D compounds are administered to said subject to provide a spectrum of activity.

15. The method of claim 14 wherein one of said at least two derivatized vitamin D compounds is calcitriol in which the hydroxy group at carbon 25 is derivatized with an acyl group.

16. A method of treating a disease in a patient in need of prolonged treatment and that responds to an active vitamin D compound, comprising selecting an in vivo hydrolyzable group such that when a hydroxy group at carbon 25 of an active vitamin D compound having a desirable in vivo therapeutic activity for treating the disease is derivatized therewith to provide a derivatized vitamin D compound, the hydrolyzable group will prolong the in vivo availability of said active vitamin D compound by regulating the in vivo rate of conversion of said derivatized vitamin D compound to said active vitamin D compound;

providing said derivatized vitamin D compound; and administering an effective dose of said derivatized vitamin D compound to a subject in need thereof.

17. The method of claim 16 wherein said derivatized vitamin D compound has a further hydrolyzable group attached at one or more of its 1, 3 or other carbon positions.

18. The method of claim 17 wherein said hydrolyzable group and said further hydrolyzable group are each independently selected from an acyl group or a hydrocarbyloxycarbonyl group.

19. The method of claim 18 wherein one or more acyl group is $CH_3CO$.

20. The method of claim 18 wherein one or more acyl group is $CH_3(CH_2)_4CO$.

21. The method of claim 18 wherein one or more acyl group is formyl.

22. The method of claim 16 wherein said active vitamin D compound is calcitriol.

23. The method of claim 16 wherein said derivatized vitamin D compound has the formula:

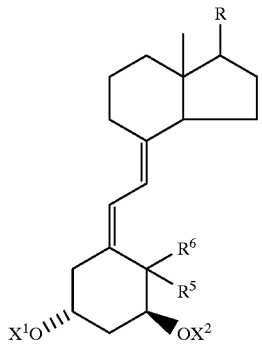

where $R^5$ and $R^6$ each represent hydrogen, or taken together $R^5$ and $R^6$ represent a methylene group, and where R is represented by the structure:

where the stereochemical center at carbon 20 in the side chain may have the R or S configuration, and where Z is selected from Y, $-OY$, $-CH_2OY$, $-C\equiv CY$ and $-CH=CHY$, where the double bond may have the cis or trans stereochemical configuration, and where Y is selected from a radical of the structure:

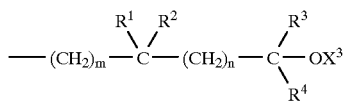

where m and n, independently, represent the integers from 0 to 5, where $R^1$ is selected from the group consisting of hydrogen, $OX^4$, fluoro, trifluoromethyl, and $C_{1-5}$-alkyl, which may be straight chain or branched and, optionally, bear a hydroxy substituent, and where $R^2$ is selected from the group consisting of hydrogen, fluoro, trifluoromethyl and $C_{1-5}$ alkyl, which may be straight-chain or branched, and optionally, bear a hydroxy substituent, and where each of $R^3$ and $R^4$, is selected from trifluoromethyl and $C_{1-5}$ alkyl, which may be straight chain or branched and optionally bear a hydroxy substituent, and where $R^1$ and $R^2$, taken together, represent an oxo group, or an alkylidene group, $=CR^2R^2$, $=CR^2R^3$, or the group $-(CH_2)_p-$, where p is an integer from 2 to 5, and where $R_3$ and $R_4$, taken together, represent the group $-(CH_2)_q-$, where q is an integer from 2 to 5, and where $X^1$, $X^2$, and $X^4$ are each hydrogen, an acyl group, or a hydrocarbyloxycarbonyl group, and where $X^3$ represents an acyl group or a hydrocarbyloxycarbonyl group.

24. The method of claim 16 wherein said derivatized compound is combined with a non-toxic pharmaceutically acceptable carrier and is administered in liquid form.

25. The method of claim 24 wherein said derivatized compound is administered by injection.

26. The method of claim 24 wherein said derivatized compound is administered intravenously.

27. The method of claim 24 wherein said derivatized compound is administered orally.

28. The method of claim 16 wherein said derivatized compound is combined with a non-toxic pharmaceutically acceptable carrier and is administered in solid form.

29. The method of claim 28 wherein said derivatized compound is administered by suppository.

30. The method of claim 28 wherein said derivatized compound is administered topically.

31. The method of claim 28 wherein said derivatized compound is administered orally.

32. The method of claim 16 wherein said disease is selected from the group consisting of renal osteodystrophy, hypoparathyroidism, pseudohypoparathyroidism, hypocalcemia, osteomalacia, vitamin D-deficient rickets, postmenopausal osteoporosis, estrogen-lack osteoporosis, senile osteoporosis, steroid-induced osteoporosis, and psoriasis.

33. The method of claim 16 wherein said derivatized vitamin D compound is administered in an amount from about 0.5 μg/day to about 10 μg/day.

34. The method of claim 16 wherein at least two derivatized vitamin D compounds are administered to said subject to provide a spectrum of activity.

35. The method of claim 34 wherein one of said at least two derivatized vitamin D compounds is calcitriol in which the hydroxy group at carbon 25 is derivatized with an acyl group.

36. A method of prolonging the duration of in vivo therapeutic activity of a biologically active vitamin D compound in a patient in need of prolonged treatment and having a hydroxy group at carbon 25, and, optionally, at carbons 1, 3 or other carbon positions, which comprises selecting one or more in vivo hydrolyzable groups such that when the hydroxy group at carbon 25, and, optionally, one or more of the hydroxy groups at carbons 1, 3 or at said other carbon positions of said active vitamin D compound is derivatized therewith to provide a derivatized vitamin D compound, the size, number or location of the hydrolyzable groups function to prolong the in vivo availability of said active vitamin D compound by regulating the in vivo rate of conversion of said derivatized vitamin D compound to said active vitamin D compound; and providing said derivatized vitamin D compound.

37. The method of claim 36 wherein said derivatized vitamin D compound has the formula:

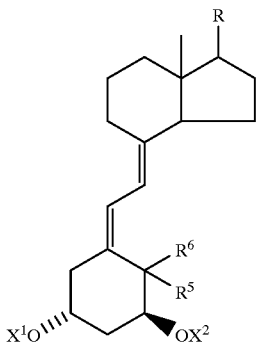

where $R^5$ and $R^6$ each represent hydrogen, or taken together $R^5$ and $R^6$ represent a methylene group, and where R is represented by the structure:

where the stereochemical center at carbon 20 in the side chain may have the R or S configuration, and where Z is selected from Y, —OY, —CH$_2$OY, —C≡CY and —CH=CHY, where the double bond may have the cis or trans stereochemical configuration, and where Y is selected from a radical of the structure:

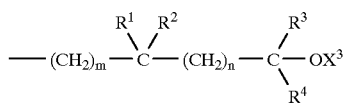

where m and n, independently, represent the integers from 0 to 5, where $R^1$ is selected from the group consisting of hydrogen, $OX^4$, fluoro, trifluoromethyl, and $C_{1-5}$-alkyl, which may be straight chain or branched and, optionally, bear a hydroxy substituent, and where $R^2$ is selected from the group consisting of hydrogen, fluoro, trifluoromethyl and $C_{1-5}$ alkyl, which may be straight-chain or branched, and optionally, bear a hydroxy substituent, and where each of $R^3$ and $R^4$, is selected from trifluoromethyl and $C_{1-5}$ alkyl, which may be straight chain or branched and optionally bear a hydroxy substituent, and where $R^1$ and $R^2$, taken together, represent an oxo group, or an alkylidene group, =CR$^2$R$^2$, =CR$^2$R$^3$, or the group —(CH$_2$)$_p$—, where p is an integer from 2 to 5, and where $R_3$ and $R_4$, taken together, represent the group —(CH$_2$)$_q$—, where q is an integer from 2 to 5, and where $X^1$, $X^2$, and $X^4$ are each hydrogen, an acyl group, or a hydrocarbyloxycarbonyl group, and where $X^3$ represents an acyl group or a hydrocarbyloxycarbonyl group.

38. The method of claim 36 wherein one or more hydrolyzable group is an acyl group.

39. The method of claim 36 wherein one or more hydrolyzable group is CH$_3$CO.

40. The method of claim 36 wherein one or more hydrolyzable group is CH$_2$(CH$_2$)$_4$CO.

41. The method of claim 36 wherein one or more hydrolyzable group is CH$_3$(CH$_2$)$_7$CO.

42. The method of claim 36 wherein one or more hydrolyzable group is a hydrocarbyloxycarbonyl group.

43. The method of claim 36 wherein said active vitamin D compound is calcitriol.

* * * * *